(12) United States Patent
Svanerudh et al.

(10) Patent No.: US 6,754,608 B2
(45) Date of Patent: Jun. 22, 2004

(54) INTERACTIVE MEASUREMENT SYSTEM

(75) Inventors: Johan Svanerudh, Uppsala (SE); Leif Smith, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 231 days.

(21) Appl. No.: 10/152,982

(22) Filed: May 23, 2002

(65) Prior Publication Data

US 2003/0033095 A1 Feb. 13, 2003

Related U.S. Application Data

(60) Provisional application No. 60/292,727, filed on May 23, 2001.

(51) Int. Cl.$^7$ ............................ G01K 1/00; G01K 11/00; G01K 13/00
(52) U.S. Cl. ............................................ 702/130
(58) Field of Search .................... 702/45, 108, 116, 702/124, 127, 130, 131; 600/504, 505, 486, 417, 549, 468

(56) References Cited

U.S. PATENT DOCUMENTS

| | | | | |
|---|---|---|---|---|
| 5,711,299 A | * | 1/1998 | Manwaring et al. | 600/417 |
| 5,954,659 A | * | 9/1999 | Curley et al. | 600/505 |
| 6,106,472 A | * | 8/2000 | Chiang et al. | 600/447 |
| 6,201,989 B1 | * | 3/2001 | Whitehead et al. | 600/476 |
| 6,231,569 B1 | * | 5/2001 | Bek et al. | 606/34 |
| 6,551,250 B2 | * | 4/2003 | Khalil | 600/505 |
| 2002/0072738 A1 | * | 6/2002 | Edwards et al. | 606/41 |
| 2002/0151804 A1 | * | 10/2002 | O'Mahony et al. | 600/504 |

OTHER PUBLICATIONS

Merl et al., Recording Diagnostic and International Procedures in the Cardia Catheter Laboratory: A Relaional Database with Graphical User Interface,Computers in Cardiology,1995,127–128.*

Ripoli et al., Integrated Instrumentation for Ventricular pressure–Volume Relationship Anaysis, Computers in Cardiology, 1995,513–516.*

* cited by examiner

Primary Examiner—John Barlow
Assistant Examiner—Demetrius Pretlow
(74) Attorney, Agent, or Firm—Foley & Lardner LLP (57) ABSTRACT

A method to assist an operator of an interactive measurement system for determining flow related parameters based upon physiological signals obtained by a measurement unit that comprises a catheter adapted to be inserted into a vessel inside a body of a human or an animal, a wire adapted to be inserted into the catheter and provided with a temperature sensor at its distal end, and a computer means adapted to receive and store detected temperature signals received from said sensor and said wire. The system further comprises a graphical user interface on a display screen connected to said computer means, wherein the method comprises the steps of:

determine if a valid activation command is received from the operator, and upon receipt of a valid activation command activate a continuous analysis of detected temperature signals, display on said graphical user interface an operator instruction in an instruction window instructing the operator to perform steps in a measurement procedure to obtain said flow related parameters, detect steps performed by the operator during the measurement procedure and display on said user interface the current status of said performed steps, display on said user interface, in real-time, temperature curves related to the measurement procedure, determine at least one flow related parameter based upon the temperature measurements obtained during said measurement procedure, display on said user interface said at least one determined flow related parameter.

14 Claims, 9 Drawing Sheets

Bas(---)  --- --- ---   Hyp(---)  --- --- ---   STOP

| EVENT/STATE /MARKER POSITION | ACTION | REC | STOP VIEW | ARROW KEYS | ESC | STATUS WINDOW |
|---|---|---|---|---|---|---|
| POS: BASELINE | CONTINUOUS PRESSURE AND TEMPERATURE, INJECTION TRIGGER NOT ACTIVE. | ENTER STATE BASELINE #1 ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | PRESS REC TO START |
| POS: BASELINE #1-3 | CONTINUOUS PRESSURE AND TEMPERATURE INJECTION TRIGGER ACTIVE. IF INJECTION DETECTED-RECORD AND DISPLAY DILUTION CURVE AND Tmn VALUE | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | INJECT |
| POS: HYPEREMIA | CONTINUOUS PRESSURE AND TEMPERATURE. INJECTION TRIGGER NOT ACTIVE. | ENTER STATE HYPEREMIA #1 ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO THERMO SUBMENU | INDUCE HYPEREMIA & PRESS REC |
| POS: HYPEREMIA #1-3 | CONTINUOUS PRESSURE AND TEMPERATURE INJECTION TRIGGER ACTIVE. IF INJECTION DETECTED-RECORD AND DISPLAY DILUTION CURVE AND Tmn VALUE | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | INJECT |
| POS: STOP | CONTINUOUS PRESSURE AND TEMPERATURE. INJECTION TRIGGER NOT ACTIVE. | ZERO TEMPERATURES | EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | PRESS STOP TO END |
| EVENT: MOVING CURSOR TO A OCCUPIED TMN SLOT. | CONTINUOUS PRESSURE AND TEMPERATURE. INJECTION TRIGGER NOT ACTIVE. | ENTER TRIGG MODE ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | PRESS REC TO REPLACE |

FIG.7A

| EVENT: ERROR, LOW INJECTION AMPLITUDE. | CONTINUOUS PRESSURE AND TEMPERATURE. CURSOR IS NOT ADVANCED TO NEXT POSITION. MESSAGE IS FLASHING TOGETHER WITH THE RE-INJECT MESSAGE. INJECTION TRIGGER ACTIVE. | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | ERROR LOW AMPLITUDE |
|---|---|---|---|---|---|---|
| EVENT: ERROR, CUTOFF TIMEOUT | CONTINUOUS PRESSURE AND TEMPERATURE. CURSOR IS NOT ADVANCED TO NEXT POSITION. MESSAGE IS FLASHING TOGETHER WITH THE RE-INJECT MESSAGE. INJECTION TRIGGER ACTIVE. | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | ERROR CUTOFF TIMEOUT |
| EVENT: ERROR, INJECTION TIME TOO LONG | CONTINUOUS PRESSURE AND TEMPERATURE. CURSOR IS NOT ADVANCED TO NEXT POSITION. MESSAGE IS FLASHING TOGETHER WITH THE RE-INJECT MESSAGE. INJECTION TRIGGER ACTIVE. | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | ERROR SLOW INJECTION |

FIG.7B-1

| EVENT: ERROR, Tmn VALUE TOO LOW. | CONTINUOUS PRESSURE AND TEMPERATURE. CURSOR IS NOT ADVANCED TO NEXT POSITION. MESSAGE IS FLASHING TOGETHER WITH THE RE-INJECT MESSAGE. INJECTION TRIGGER ACTIVE. | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | ERROR Tmn VALUE TOO LOW |
|---|---|---|---|---|---|---|
| EVENT: SECOND IMAGE WHEN INJECTION ERROR HAS OCCURRED. | CONTINUOUS PRESSURE AND TEMPERATURE. CURSOR IS NOT ADVANCED TO NEXT POSITION. MESSAGE IS FLASHING TOGETHER WITH THE ERROR MESSAGE. INJECTION TRIGGER ACTIVE. | ZERO TEMPERATURES | PROMPT USER, EXIT CFR, SAVE DATA TO DISK AND DISPLAY CFR-VIEW | MOVE TO ANOTHER STATE | PROMPT USER FOR CONFIRMATION. EXIT CFR AND MOVE TO OPTIONS SUBMENU | INJECT AGAIN! |
| EVENT: INJECTION DETECTED | CONTINUOUS PRESSURE AND TEMPERATURE. MESSAGE DISPLAYED UNTIL INJECTION IS FINISHED. | NO ACTION | NO ACTION | NO ACTION | PROMPT USER FOR CONFIRMATION. EXIT CFR AND MOVE TO OPTIONS SUBMENU | WAIT |

INTERACTIVE MEASUREMENT SYSTEM

CROSS-REFERENCE TO RELATED PATENT APPLICATIONS

This application claims priority to U.S. provisional application Serial No. 60/292,727, filed May 23, 2001. The contents of this provisional application are incorporated herein by reference.

FIELD OF THE INVENTION

This invention relates to flow measurements in narrow channels in general, and in particular to in vivo flow measurements in blood vessels using a method in an interactive system. The invention is applicable when performing coronary flow reserve (CFR) measurements and also when performing fractional flow reserve (FFR) measurements, each taken separately or in combination.

The invention also relates to an interactive graphical user interface and a computer program executing program instructions applicable for performing the method.

BACKGROUND OF THE INVENTION

In order to measure flow in very narrow channels such as blood vessels, it has been known for a long time to employ a number of different methods, e.g. the so called timed venous collection technique, electromagnetic flow measurements, epicardial ultrasonic flow velocity measurement, the thermodilution technique, and other techniques. For details on these techniques, reference is made to "Maximal Myocardial Perfusion as a Measure of the Functional Significance of Coronary Artery Disease", by N. H. J. Pijis, (1991), Cip-Gegevens Koninklijke Bibliotheek, den Haag, (ISBN 90-9003818-3).

The present invention concerns improvements in the operation and control of the thermodilution principle, and therefore this principle will be briefly summarized below.

Application of the thermodilution principle in the coronary sinus was introduced by Ganz (Ganz et al, "Measurement of coronary sinus blood flow by continuous thermodilution in man, *Circulation* 44:181–195, 1971). A small catheter is introduced deeply into the coronary sinus and cold saline is delivered at its tip. Theoretically, flow can be calculated from the changes in blood temperature, registered by a thermistor close to the outlet of the coronary sinus. An advantage of this method is that only right heart catheterization is required.

The principle of thermodilution involves injecting a known amount of cooled liquid, e.g. physiological saline in a blood vessel. After injection the temperature is continuously recorded with a temperature sensor attached to the tip of a guide wire that is inserted in the vessel. A temperature change due to the cold liquid passing the measurement site, i.e. the location of the sensor, will be a function of the flow.

There are various methods of evaluating the temperature signal for diagnostic purposes. Either one may attempt to calculate the volume flow, or one may use a relative measure, where the flow in a "rest condition" is compared with a "work condition", induced by medicaments.

The latter is the simpler way, and may be carried out by measuring the width at half height of the temperature change profile in the two situations indicated, and forming a ratio between these quantities.

Another way of obtaining a ratio would be to measure the transit time from injection and until the cold liquid passes the sensor, in rest condition and in work condition respectively.

The former method, i.e. the utilization of the volume flow parameter as such, requires integration of the temperature profile over time in accordance with the equations given below $$Q_{rest} = V \Big/ \int_{t_0}^{t_1} (T_{r,m}/T_{r,l}) dt \propto V \Big/ \int_{t_0}^{t_1} (T_{r,0} - T_{r,m}) dt \quad (1)$$

$$Q_{work} = V \Big/ \int_{t_0}^{t_1} (T_{w,m}/T_{w,l}) dt \propto V \Big/ \int_{t_0}^{t_1} (T_{w,0} - T_{w,m}) dt \quad (2)$$

wherein

V is the volume of injected liquid
$T_{r,m}$ is the measured temperature at rest condition
$T_{r,l}$ is the temperature of injected liquid at rest condition
$T_0$ is the temperature of the blood, i.e. 37° C.
$T_{w,m}$ is the measured temperature at work condition
$T_{w,l}$ is the temperature of injected liquid at work condition
Q is the volume flow These quantities may than be used directly for assessment of the condition of the coronary vessels and the myocardium of the patient, or they may be ratioed as previously to obtain a CFR, i.e. $CFR = Q_{work}/Q_{rest}$.

The latter method, i.e. determination of the transit time requires an accurate time measurement, in view of the relatively small distances in question, about 10 cm or less from injection to measurement site.

E.g. in order to obtain a correct measurement, the time has to be measured with some accuracy. Using a simple stopwatch, which is a common means of timing, is far too inaccurate for obtaining reliable transit times.

The flow F may be obtained as follows, which is a derivation for a similar technique, namely the indicator dilution technique. This is based on a rapidly injected amount of some kind of indicator, the concentration of which is measured.

For this purpose, the function h(t) is introduced which is the fraction of indicator, passing per unit of time at a measurement site at time t. In other words, h(t) is the distribution function of transit times of the indicator particles. If it is assumed that that flow of the indicator is representative for flow of the total fluid (complete mixing), h(t) is also the distribution function of transit times of all fluid particles. Suppose the total volume of fluid is made up of a very large number of volume elements $dV_i$ which are defined in such a way that $dV_i$ contains all fluid particles present in the system at t=0, with transit times between $t_i$ and $t_{i+1}$. The fraction of fluid particles requiring times between $t_i$ and $t_{i+1}$ to pass the measurement site, is $h(t_i) \Delta t$ by definition, and because the rate at which the fluid particles pass at the measurement site, equals F, the rate at which the particles making up $dV_i$ pass at the measurement site is $F \cdot h(t_i) \cdot \Delta t$. The total volume of $dV_i$ equals the time $t_i$, required for all particles segments in $dV_i$ to pass at the measurement site multiplied by the rate at which they leave. In other words:

$$dV_i = t_i \cdot F \cdot h(t_i) \cdot \Delta t$$

and by integration:

$$V = F \int_0^\infty t \cdot h(t) dt$$

The integral in the equation above represents the mean transit time $T_{mn}$, which is the average time, needed by one particle to travel from an injection site to a measurement site. Therefore:

$$V = F \cdot T_{mn}$$

or:

$$F = V/T_{mn}; \quad T_{mn} = V/F$$

which states the fundamental fact that flow equals volume divided by mean transit time.

Although the above derivation was made for the mentioned indicator dilution technique, the result is the same for thermo-dilution since the same distribution function may be employed.

RELATED PRIOR ART

Applicant's own International Patent Application WO 97/27802 entitled "Combined flow, pressure and temperature sensor", and filed Jan. 30, 1997, discloses a combined pressure, temperature and flow sensor. Therein, the utility of the combined sensor is discussed in terms of application of the hot anemometer technique, and the thermodilution technique.

However, the time measurement is triggered by the cold saline passing a temperature sensor at a point upstream of the measurement point. This requires a special guide catheter provided with a temperature sensor.

U.S. Pat. No. 6,089,103, also assigned to the same applicant as the present application and relates to a method of flow measurements in a narrow channel. A sensor is provided, having an element sensitive to pressure, and an element sensitive to a selected chemical or physical property, e.g. temperature. When a thermo-dilution measurement is to be performed a guide catheter is filled entirely all the way up to the distal opening with cold saline, at a temperature lower than the blood temperature. Then a small bolus amount is injected into the guide catheter, normally at its proximal end. Thereby a corresponding amount will be expelled from the distal opening of the guide catheter and into the blood vessel, and thereby transported towards the measurement point by the flowing blood. When the cold saline passes a temperature sensor on the distal tip of the guide catheter, the temperature sensor registers a temperature gradient and in response thereto a timer in a control unit is initiated. Again, when the bolus of cold saline passes the sensor at the distal tip of the guide wire, a temperature gradient is recorded and the software in a control unit processes the recorded data and outputs a result a value of a flow parameter.

EP-1,125,548 (published after the priority date of the present application) relates to measurement of flow in blood vessel by thermo-dilution and in particular to a method of triggering such measurement in order to improve the measurements. In the EP-application the inventors have realized that a previous problem acknowledged in connection with thermo-dilution can be used to an advantage for triggering purposes. Namely, when a bolus of cold saline is injected into a catheter where a wire carrying the sensor unit and electrical leads for signal transmission is located, the lead resistance will be instantly affected by the cold saline by a change in the resistivity. This is a problem in that the change must be compensated for in order to arrive at a correct output signal. In accordance with the invention in the EP-1,125,548, the resistivity change is recorded as a resistance variation curve, and various parts of the recoded curve, or the entire curve, can be mathematically processed to give as a result a starting point for the determination for a transit time of the injected liquid. The starting point can be determined in different ways. According to one way the onset of the resistivity reduction is registered and the derivative of the curve is calculated, and if the derivative exceeds a preset value, time measurement is triggered. Another way is to use the peak value as a stating point for time measurement. Again the derivative, or preferably the second derivative, is calculated and the change in sign is detected. In this way the accuracy in the time measurement is significantly improved.

In order to take full advantage of the improved accuracy in the time measurement which of course also influences the overall measurement accuracy of CFR and also FFR the physician performing the diagnostic measurements must be able to easily and safely be guided through the measurement procedure, and also have the relevant measurement results presented in a way that gives a clear overview of all aspects of the results.

SUMMARY OF THE INVENTION

The object of the present invention is to achieve an improved method in a flow measurement system including an improved interactive user interface.

The above-mentioned object is achieved by a method according to the independent claim.

Preferred embodiments are set forth in the dependent claims.

DETAILED DESCRIPTION OF THE PREFERRED EMBODIMENTS

Figure 1:
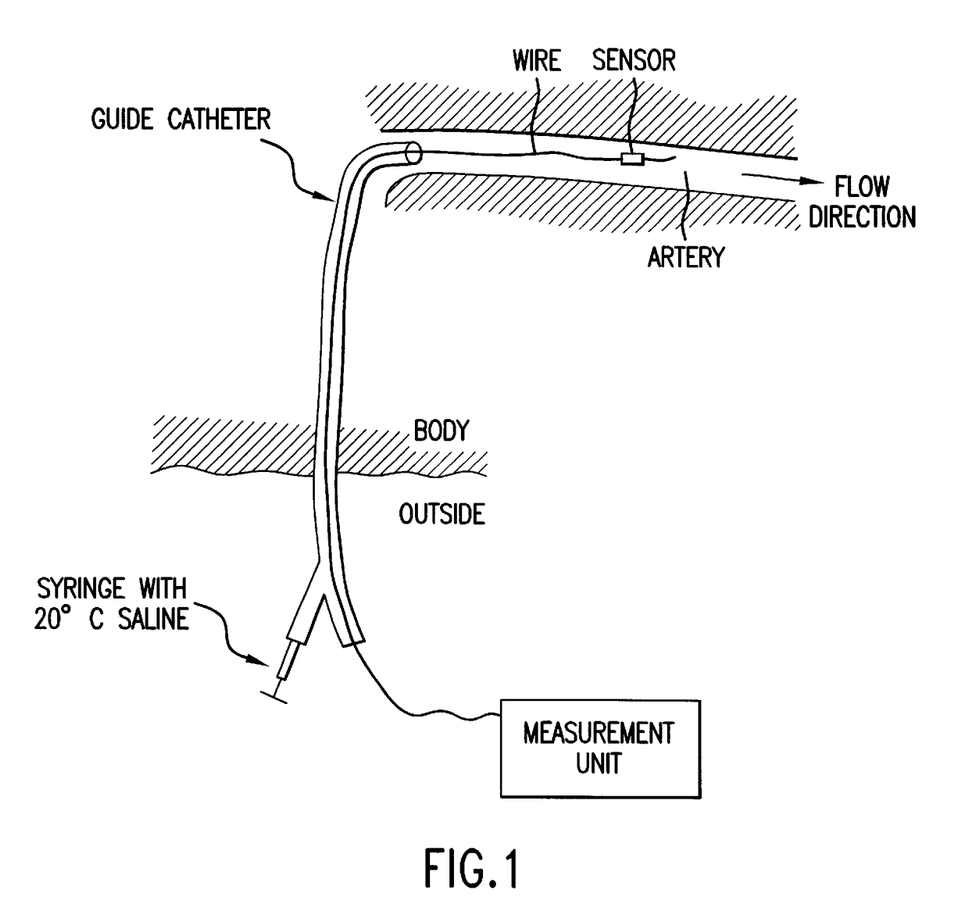
FIG. 1 schematically illustrates the measurement technique where the method according to present invention is applicable.

FIG. 1 schematically illustrates the measurement technique where the method according to present invention is applicable.

In FIG. 1 there is disclosed a system suitable for implementation of the present invention. The system comprises a hollow guide catheter insertable into the body of a patient, the distal end of which functions as an outlet for liquid to be passed there through. The catheter is located at a point in a region in the artery system where it is desired to determine the flow. Inside the catheter a wire is inserted, the distal end of which carries a sensor unit having a temperature sensor and optionally a pressure sensor. Other additional sensors are also conceivable, e.g. pH sensors, ion selective sensors etc. The wire is extended past the distal end of the catheter such that the sensor unit is located at a relatively small distance, e.g. 10 cm, from the catheter outlet.

Alternatively, the wire can be inserted as above and positioned in an appropriate position, and then a second catheter is passed over the wire, inside the guide catheter and the distal end of this second catheter is positioned in the artery system where it is desired to know the flow. The first catheter will thereby only be used for guiding. This alternative approach can be used if the vessel tree is fairly complex with many narrow blood vessels, such that it can be difficult to position a catheter without the help of the wire.

The guide catheter (or the second catheter in the alternative) is provided at the proximal end with an inlet for saline. Suitably a Luer® lock is provided in order that a syringe easily be connected. The sensor unit is coupled to a measurement unit for the processing of the signals from the sensor, said signals being transferred via electrical leads running along the wire.

The measurement unit comprises a computer means, operable via a remote control, and a display screen for a graphical user interface showing e.g. recorded graphs and calculated values of the measurements. The graphical user interface also includes menus from which the desired functions are selectable via the remote control. There is also a memory function for storing recordings, so as to be able to refer back to old measurements.

Figure 2:
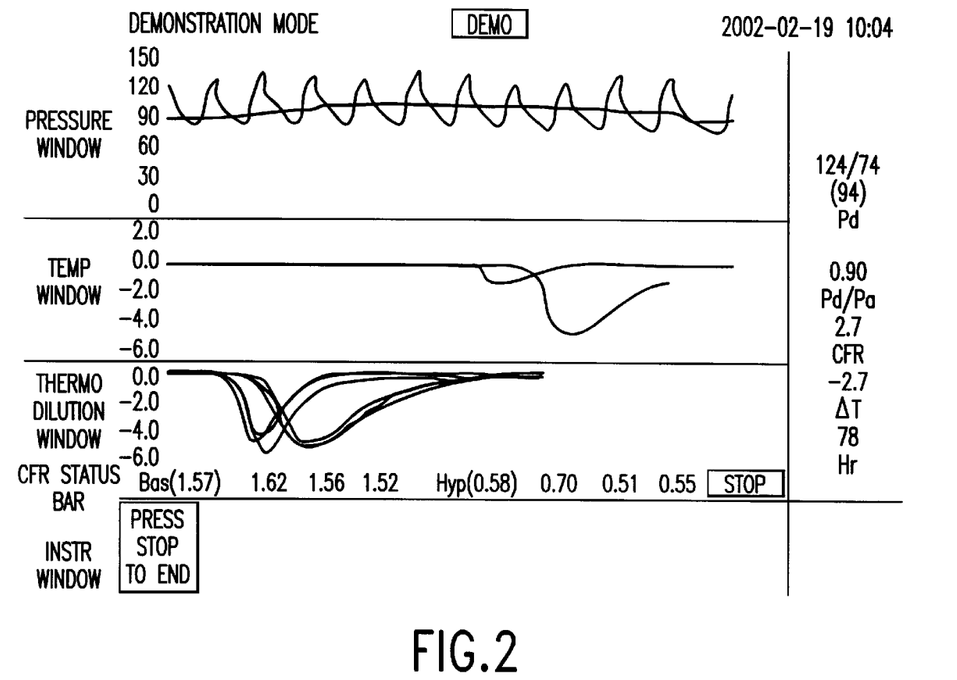
FIG. 2 shows a graphical user interface (GUI) according to a preferred embodiment of the present invention.

FIG. 2 shows a graphical user interface (GUI) according to a preferred embodiment of the present invention.

The graphical user interface according to the preferred embodiment comprises the following main parts (it should be noted that the relative positions illustrated in the figure is only an illustrating example):

Below the title bar at the top is a pressure window where pressure curves are shown if a pressure sensor is used. The two curves are the arterial pressure ($P_a$) (having higher amplitudes) and the distal coronary hyperemic pressure ($P_d$). Information from theses pressure curves is used to calculate the fractional flow reserve (FFR), which is the ratio between Pd and $P_a$. This will be further discussed below.

In the temperature window the real-time temperature curves for the wire (or cable) and the temperature sensor are displayed. The wire first detects the drop in temperature and that curve also has a smaller temperature drop than for the sensor.

The window below the temperature window is the thermodilution window where temperature curves obtained from the temperature sensor during the measurement procedure are displayed. In this example six curves are displayed where three reflects the condition during hyperemia.

The vertical axes for the temperature window and thermodilution window indicate the temperature differences.

Figure 3:
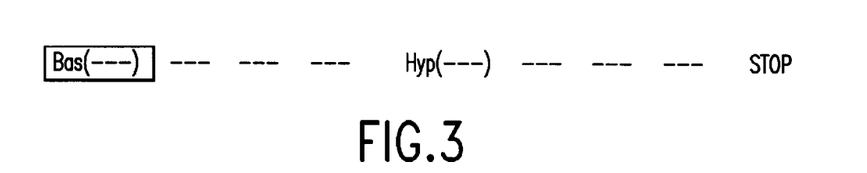
FIG. 3 shows CFR status bar in the GUI.

Below the thermodilution window is the CFR status bar (see also FIG. 3) that visualizes the CFR recording sequence by indicating which state the instrument is currently in and displaying the calculated Transit mean time ($T_{mn}$) values. Current state is indicated by a green rectangle. As the green rectangle moves through the cycle the status window displays a flashing information image, connected to each state.

There are six memory slots for storing $T_{mn}$-values, three during baseline (normal) conditions and three during hyperemia. Next to the Bas and Hyp texts is an averaging slot where the average of the three values is automatically displayed in brackets as soon as there is one or more $T_{mn}$-values stored. When there is at least one Bas (before hyperemia) $T_{mn}$ and one Hyp (during hyperemia) $T_{mn}$ stored; a CFR ratio is calculated. The averages and the ratio are updated each time a new measurement is recorded. The CFR ratio is displayed in a window to the right in the GUI, in this example the CFR ratio is 2,7. The averages and the ratio are updated each time a new measurement is recorded. Also displayed in the right window are the temperature difference ($\Delta T$) and the heart rate (Hr).

An instruction window is shown in the lowest left corner; in this window different operator instructions are displayed.

To the right of the instruction window may different menus be displayed, which are not shown in this view.

In the following a measurement procedure according to the preferred embodiment of the present invention will be described.

The CFR functionality enables the system to repeatedly measure sensor and cable temperature cycles in order to determine the flow ratio CFR. The CFR ratio is calculated using several separated thermodilution measurements before and during hyperemia. The hyperemia state, or "work condition", is induced by medicaments.

From each measurement a key value, the so-called "transit mean time", $T_{mn}$, is calculated and stored. The $T_{mn}$ values before and during hyperemia are averaged and a ratio is calculated.

Baseline

When the CFR mode is activated the screen presents continuous pressure and temperature. The temperature is zeroed. The "Bas" position is highlighted and the user is prompted to press REC at the remote control to start the recording. The trigger is not activated in this mode.

Base 1–3

To start the recording sequence the user presses REC on the remote control. The first baseline position is then highlighted in green and the status window displays the message for that state.

The instrument is now waiting for an injection of cold saline, indicated by a sudden drop in cable and sensor temperature. The drop is automatically detected and the following sequence is recorded. When the temperature has returned to normal the recording is automatically stopped and the thermodilution curve and $T_{mn}$ value is displayed beneath the real-time temperature graph. The highlighted position is automatically advanced to the next position.

Hyperemia

After three baseline injections the "Hyp" position is highlighted. In this state the trigger is inactivated and the user is prompted to press REC again to continue with the hyperemia recordings after hyperemia is induced.

Hyp 1–3

In a similar way as in the base 1–3 states the instrument awaits the saline injections and automatically displays $T_{mn}$ values and dilution curves.

Stop

When the last hyperemia injection has been made the cursor is advanced to the Stop position. Here the user is prompted to press STOP/VIEW to exit CFR mode and go to the CFR VIEW screen where pressure and dilutions curves are displayed.

Generally the cursor is automatically moved from one state to another, without any user interaction. It is though possible to manually move the cursor from one state to another using arrow keys on the remote control. Moving the cursor manually to a $T_{mn}$ slot that has already been recorded will set the instrument in a wait state where the user is required to press REC to enter the trigger mode. If an injection then is recorded then the old dilution value will be overwritten. However, if the slot is not "occupied" then the instrument automatically enters trigger mode.

When the CFR mode is activated the first storage position in Base measurement is highlighted using a green rectangle (see display image above at the horizontal line with "Base" to the left, close to the bottom). The user can move the highlighted position using the left and right keys on the remote control and thus change the position where the following $T_{mn}$-value will be stored.

If the trigger detects an erroneous injection the status message window displays a flashing alternating error message and a "Re-inject" message. The instrument is now waiting for the user to try the injection again.

The system according to the present invention is adapted to handle calculation and presentation of coronary flow reserve (CFR). The user interface shown above and in the following is adapted for use when presenting results from temperature measurements isolated or in combination with pressure measurements.

Figure 4:
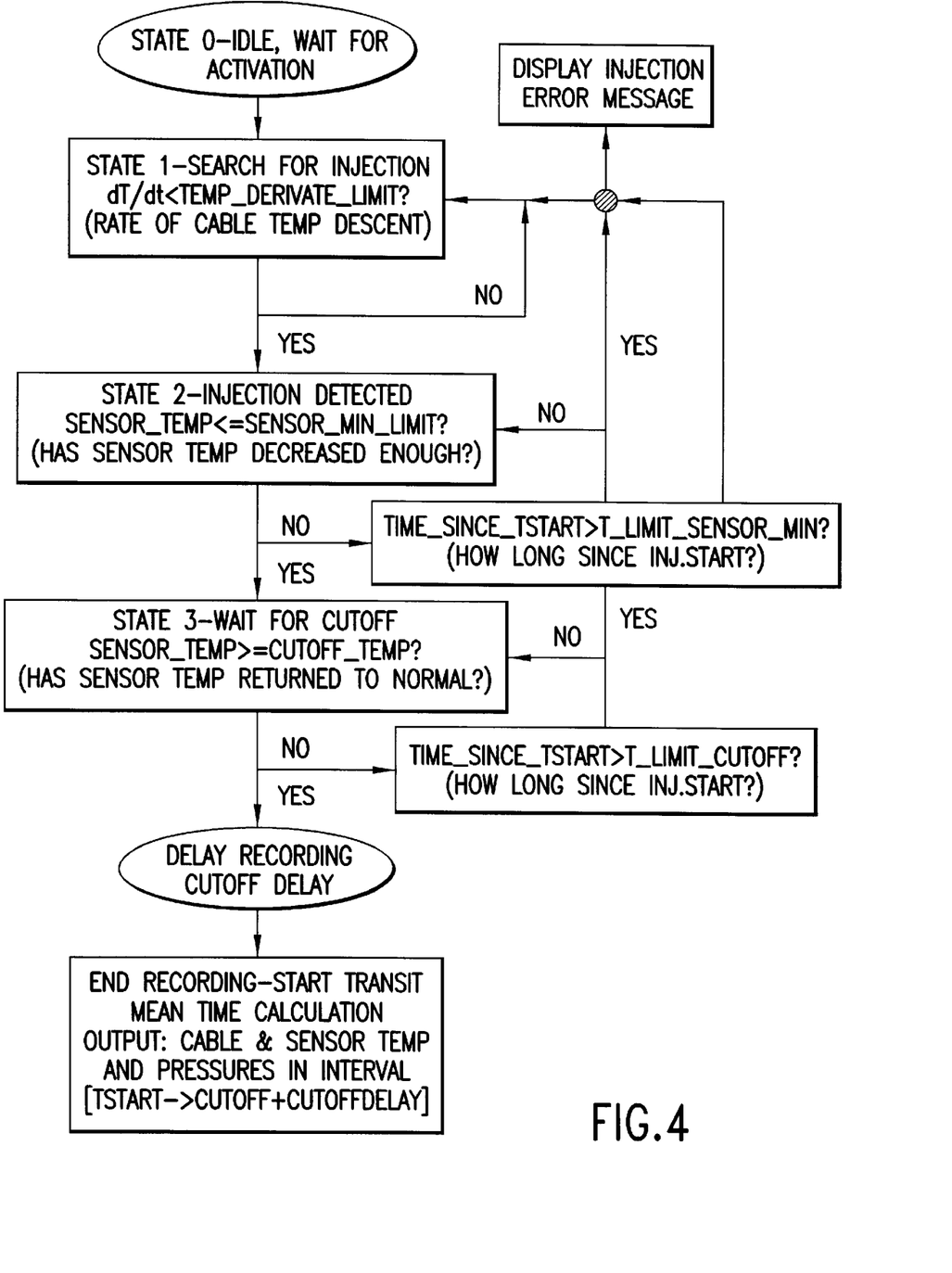
FIG. 4 shows a flowchart illustrating the method according to the preferred embodiment of the present invention.

FIG. 4 shows a flowchart illustrating the method according to the preferred embodiment of the present invention.

Figure 5:
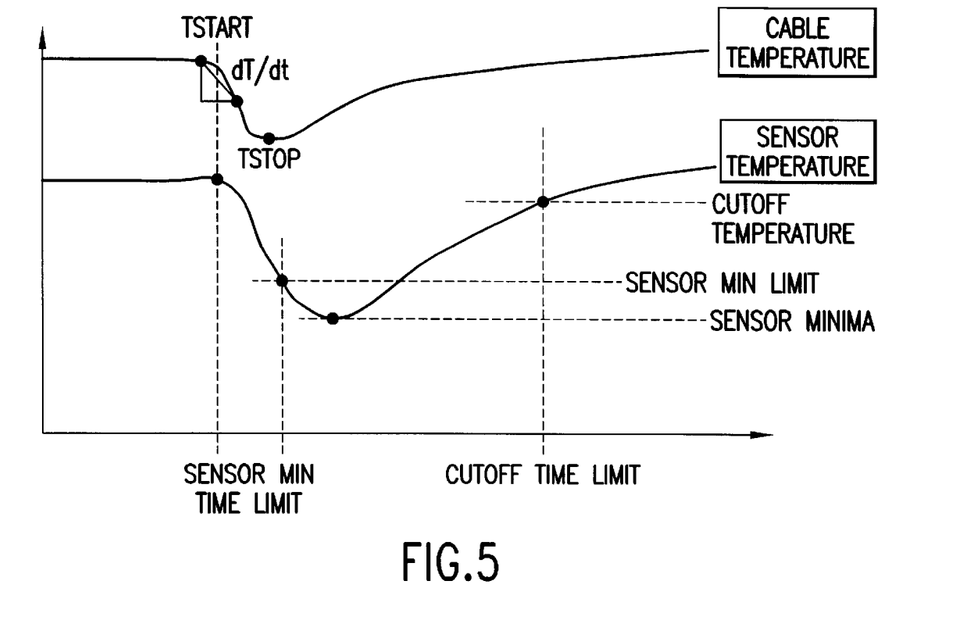
FIG. 5 the saline injection trigger is illustrated by showing the temperature curves of the wire and the sensor.

Table 1 includes short descriptions of the variables used in the flowchart of FIG. 4 and also in FIG. 5.

In FIG. 5 the saline injection trigger is illustrated by showing the temperature curves of the wire (cable) (above) and the sensor (below).

The injection trigger shall continuously search an incoming stream of temperature data from the wire and the sensor in order to detect a cold-water injection, indicated by a sudden temperature drop, and record data during the injection until the temperature has returned to a fraction of its original value.

The algorithm is robust in the sense that it does not accept injections that are too slow, does not reach a minimum value or does not return to a set fraction of its original value within a given time.

TABLE 1

| Variable | Description |
| --- | --- |
| dT/dt | Cable temperature derivative, length 15 samples (100 Hz) |
| temp_derivate_limit | Trigger limit, cable temp descent, 0.50 (500 units) |
| sensor_min_limit | Minimum temperature sensor must decrease during injection, −1.00 (1000 units) from sensor[Tstart]. |
| Tstart | Start of injection (mid-position in derivative buffer when trig point reached) |
| Tstop | End of injection (minimum position in cable temperature) |
| inj_time_limit | Injection time, Tstop–Tstart, max 0.6 seconds |
| Time_since_Tstart | Time since Tstart |
| Sensor min time limit | Maximum time between Tstart and when temp min limit should have been reached. 4 s (400 samples, 100 Hz) |
| Cutoff_temp | Point where sensor temperature has returned to normal. 0.10 * (sensor_minima) (sensor_minima is searched for after temp_min_limit has been passed.) |
| Cutoff time limit | Maximum time between Tstart and when cutoff_temp should have been reached. 8 s (800 samples, 100 Hz) |
| cutoff _delay | Recording time after cutoff temp has been reached and before recording is turned off. 5s-time_since_Tstart |
| Tmn_baseline_limit | Lower limit on Tmn value calculated in baseline conditions, 0.5 seconds. |
| Tmn_hyperemia_limit | Lower limit on Tmn value calculated in hyperemia conditions, 0.1 seconds. |

Returning to FIG. 4 the method is in its idle state 0 where it waits for activation from the operator, e.g. via the remote control.

When an activation command is entered method is in state 1 where the real-time injection trigger is activated. The trigging may be performed by e.g. calculating the derivative dT/dt of the cable temperature curve and when the rate of cable temperature descent reaches a predetermined limit an injection is considered to be detected and the method enters state 2.

In state 2 it is determined if the sensor temperature has decreased enough to be considered as an acceptable injection.

If the sensor temperature not has decreased enough state 2 continuous until a predetermined time has elapsed and if the temperature then has not decreased enough the method returns to state 1.

If the sensor temperature has decreased enough state 3 is entered where it is determined when the sensor temperature is above a cutoff temperature.

If this takes too long time the method returns to state 1.

When the sensor temperature is higher than the cutoff temperature the cutoff delay is recorded and the method enters the end recording state where the transit mean time calculation is performed. The result obtained from the interval (Tstart–cutoff+cutoff delay) is presented at the graphical user interface as temperature curves for the sensor.

Figure 6:
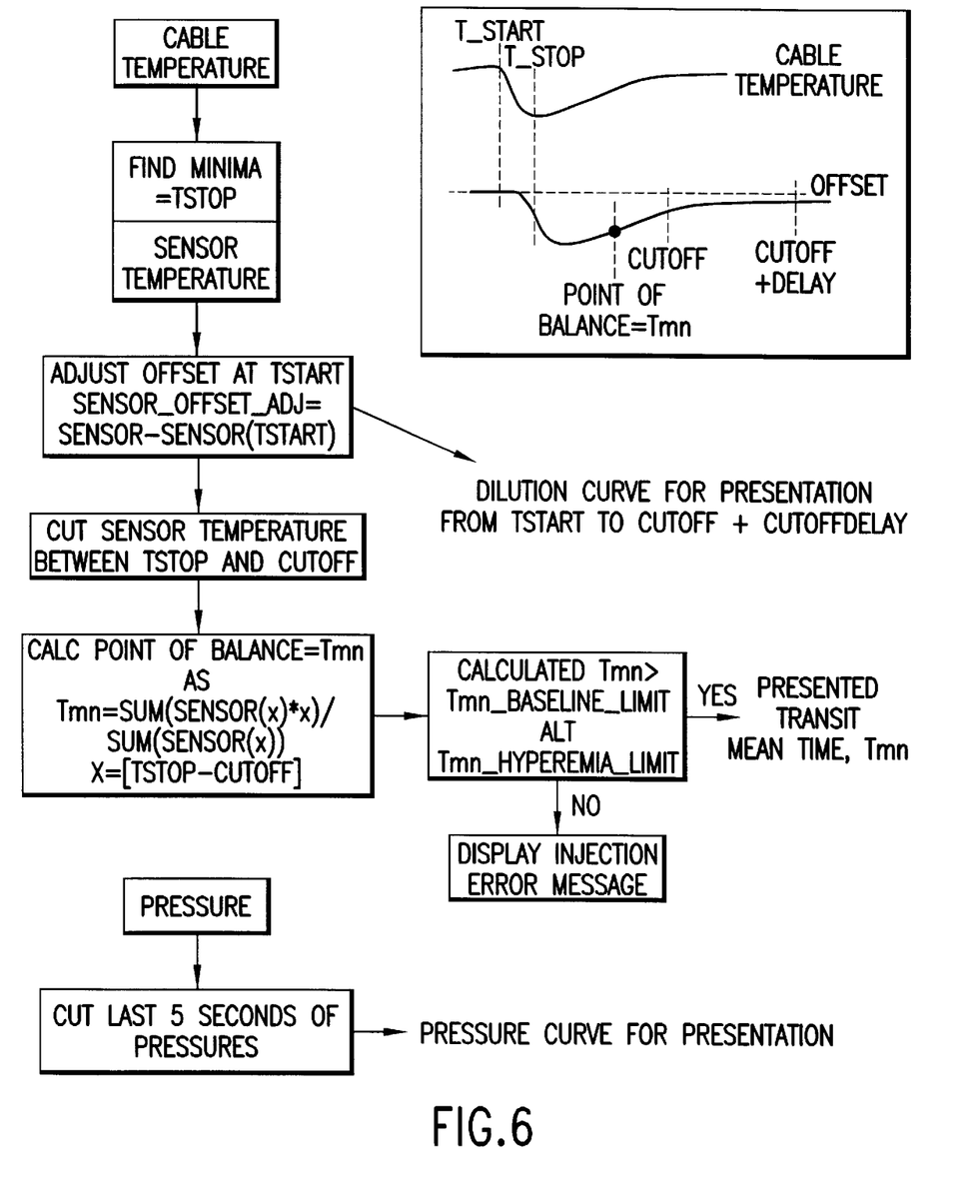
FIG. 6 is another flowchart illustrating, at a higher level, the preferred embodiment of the present invention.

FIG. 6 is another flowchart illustrating, at a higher level, the preferred embodiment of the present invention.

The right part of FIG. 6 shows curves of the cable temperature and the sensor temperature.

In the flowchart, the cable temperature is detected and monitored in order to find $T_{start}$ being determined as indicated above by calculating the derivative of the curve. $T_{start}$ is used to adjust an offset level for the sensor signal. The sensor temperature between $T_{stop}$, determined as the minimum of the cable temperature curve and $T_{mn}$ is then calculated using the formula set forth in the flowchart. If the calculated $T_{mn}$ fulfils the criteria given in table 1 it is presented in the CFR status bar of the GUI.

Also the generation of the dilution curves is indicated in the flowchart.

According to a second preferred embodiment of the present invention the wire is provided with a pressure sensor at the distal tip close to the temperature sensor. A further advantage with the present invention is that also pressure measurements are performed simultaneously with the temperature measurements and then also presented at the GUI as indicated above. In FIG. 6 a short flowchart illustrates this.

Figure 7B:
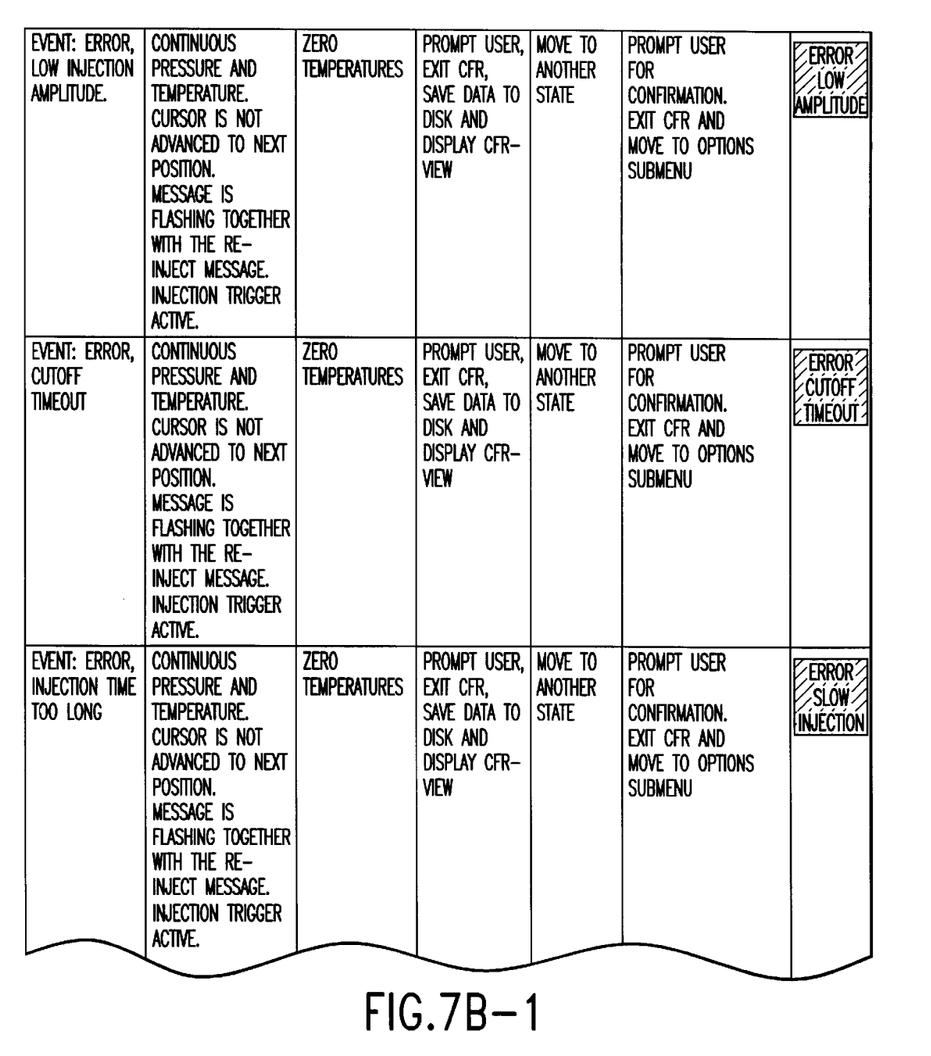
FIGS. 7a and 7b show a set of different states and their respective status window that may be shown on the graphical user interface with their respective description.
Figure 7B:
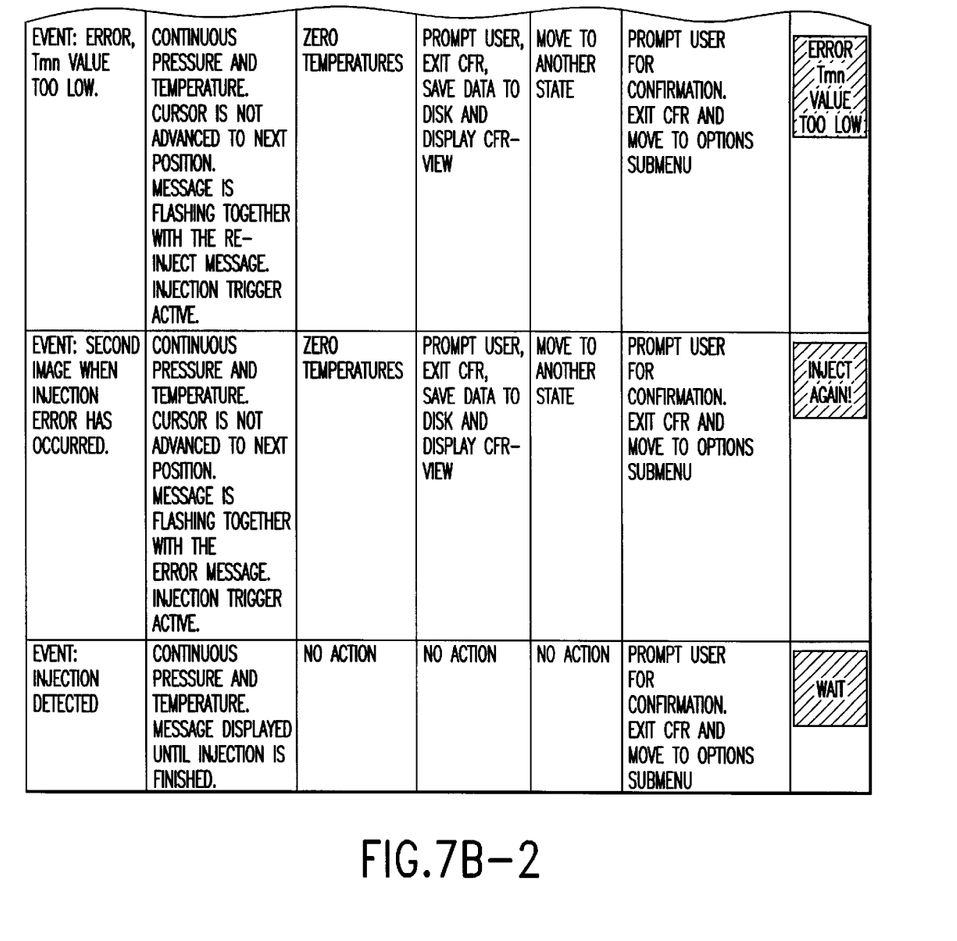

FIGS. 7a and 7b show a set of different states and their respective status window that may be shown on the graphical user interface with their respective description.

The columns from left relate to the event/state/marker position and a description of the Action. The columns REC, STOP/VIEW, Arrow keys and ESC all comprise in short words what will happen when any of these is activated at the remote control when on a line of specific status information displayed in the Status window.

FIG. 7b relates to different error messages and how these are handled.

Figure 8:
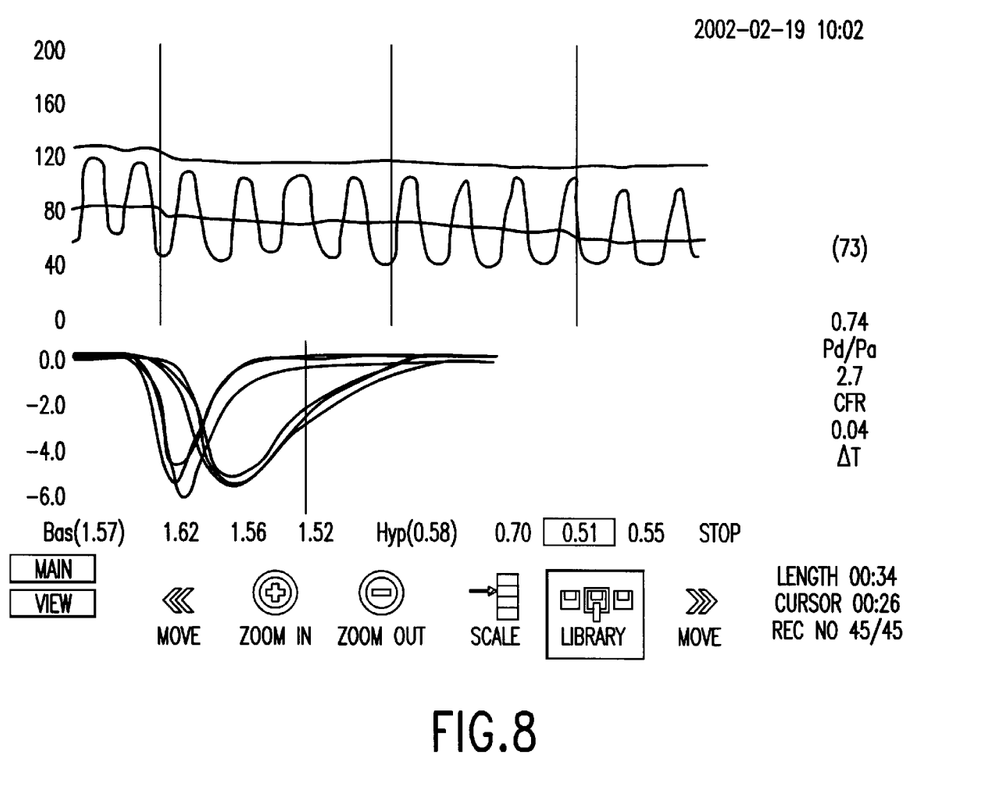
FIG. 8 shows a view at a higher level of the graphical user interface (GUI) according to a preferred embodiment of the present invention.

FIG. 8 shows a view at a higher level of the graphical user interface (GUI) according to a preferred embodiment of the present invention. This view includes the pressure window, the thermodilution window, the CFR status bar and also the right part where various calculated values are displayed. In the lower part of the GUI different tools needed for navigation within the system are shown.

In the preferred embodiment described above the measurement procedure is automatically performed with only a minimum of operator actions to be performed. According to the method the system awaits an injection to be performed by the operator and then automatically performs the necessary steps in order to accept the injection, measures the necessary times needed to perform the calculations of the requested parameters and automatically records and displays curves of interest in an user-friendly environment.

In the following an alternative embodiment of the present invention will be described. This embodiment involves more action steps to be performed by the operator, but the results obtained by using this embodiment are equally useful and may be displayed in the GUI described above in connection with the preferred embodiment.

When the REC button on the remote control is pressed the recording of the thermo dilution measurement starts. During recording, the sensor temperature is displayed in real-time. When the cycle is finished (by pressing stop/view on the remote or by end-cycle trigger) recording stops and the recorded sensor signal is drawn on screen. The $T_{mn}$-value for the recording is calculated and displayed in the CFR status window. Each recorded sensor signal is drawn on top of the previous measurements in a color depending on whether the measurement was before or during hyperemia. There can be a total of six sensor recordings in the same window. After one recording the user presses ESC to return to continuous temperature measurement again.

Below follows a short description of the alternative method.

The operator records short sequences of sensor and cable temperature. Each sequence is ended when the user presses STOP after which the system calculates and presents the $T_{mn}$ value for the sequence. The system also calculates and presents the sensor signal, offset adjusted and normalized.

During recording a green "REC" symbol is flashing in the menu-tree window.

After each recording cycle the highlighted position is automatically moved forward one step until it reaches the third Hyper-position where it stops. If the cursor is moved to a position where there already is a recording stored and the REC button is pressed, that recording is erased and replaced by the new one. In order to erase a stored recording and its $T_{mn}$ value, the cursor is moved to the position of the recording and the ENTER button is kept pressed for 3 seconds.

To exit CFR-mode and save the whole measurement sequence, the user presses ESC on the remote control. The user is then prompted if he wants to save measurement and exit or return to CFR.

Preferably six measurements are performed, three before and three during hyperemia, and corresponding calculated $T_{mn}$ values are displayed in the CFR status window. The calculated CFR value is displayed in the right window (see e.g. FIG. 2).

When the user leaves the CFR mode the whole measurement is stored on disk using the patient identity, date and time as unique identifiers. Data stored on disk are all recorded temperature measurements, both sensor and cable signals, and the calculated $T_{mn}$ and CFR values. This is also applicable for the preferred embodiment of the present invention.

As indicated above a very advantageous second preferred embodiment of the present invention is to include, in addition to the temperature sensor, a pressure sensor at the distal end of the wire. It will then also be possible during the same state of hyperemia to perform pressure measurements and as shown in e.g. FIG. 2 pressure curves may be displayed and a very useful parameter, the fractional flow reserve (FFR), may be calculated and displayed.

The pressure values detected during each injection during a measurement procedure is recorded, displayed and stored. The pressure obtained during a state of hyperemia may e.g. be used to confirm that all three saline injections performed during a measurement procedure were performed during the same state of hyperemia. Another advantageous use of the pressure measurements is to be able to calculate the Fractional Flow Reserve (FFR) being the ratio between $P_d$ and $P_a$. The lowest value for the ratio during a three-injection hyperemia measurement procedure is set as the FFR-value.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A method to assist an operator of an interactive measurement system for determining flow related parameters based upon physiological signals obtained by a measurement unit, said measurement unit comprises a catheter adapted to be inserted into a vessel inside a body of a human or an animal, a wire adapted to be inserted into the catheter and provided with a temperature sensor at its distal end, and a computer means adapted to receive and store detected temperature signals received from said sensor and said wire, characterized in that said system further comprises a graphical user interface on a display screen connected to said computer means, wherein the method comprises the steps of:

determine if a valid activation command is received from the operator, and upon receipt of a valid activation command activate a continuous analysis of detected temperature signals, display on said graphical user interface an operator instruction in an instruction window instructing the operator to perform steps in a measurement procedure to obtain said flow related parameters, detect steps performed by the operator during the measurement procedure and display on said user interface the current status of said performed steps, display on said user interface, in real-time, temperature curves related to the measurement procedure, determine at least one flow related parameter based upon the temperature measurements obtained during said measurement procedure, display on said user interface said at least one determined flow related parameter.

2. Method according to claim 1, characterized in that said measurement procedure comprises the following steps:

instructing the operator to perform an injection step a predetermined number of times when an operator instruction "INJECT" is displayed, wherein said injection step includes performing an injection of a liquid into said vessel via the catheter, and instructing the operator to perform an induce hyperemia step when an operator instruction "INDUCE HYPEREMIA" is displayed, wherein said induce hyperemia step includes performing an injection of a medicament into the human or animal in order to set the human or animal in a state of hyperemia.

3. Method according to claim 1, characterized in that one of said flow related parameters is coronary flow reserve (CFR), which is calculated as the ratio between flow related values before and during hyperemia is induced.

4. Method according to claim 1, characterized in that said wire is also provided with a pressure sensor at the distal end of the wire, wherein said computer means is adapted to receive and store detected pressure signals received from said pressure sensor.

5. Method according to claim 4, characterized in that one of said flow related parameters is fractional flow reserve (FFR), which is calculated by using the detected pressure signals.

6. Method according to claim 4, characterized in that said method comprises the further step:
   display on said user interface, in real-time, pressure curves related to the measurement procedure.

7. Method according to claim 2, characterized in that CFR and FFR are calculated during the same period of hyperemia.

8. Method according to claim 1, characterized in that said continuous analysis of detected temperature signals includes determining a starting point of the analysis of the sensor temperature signal based upon analysis of a signal representing the temperature of said wire.

9. Method according to claim 8, characterized in that said signal representing the temperature of said wire is the electrical resistance of said wire.

10. Method according to claim 1, characterized in that said analysis of the signal representing the temperature of said wire includes the step of applying predefined cable temperature criteria on said signal, and when said temperature criteria is fulfilled an accepted detection is acknowledged and a starting point for analysis of the sensor temperature signal is determined.

11. A graphical user interface for use in connection with an interactive measurement system, characterized in that said interface is adapted to display operator instructions, curves and calculated values obtained by the method according to claim 1.

12. A computer program comprising computer executable instructions:
   for causing a computer to generate the graphical user interface according to claim 11 on a display screen.

13. A computer program comprising computer executable instructions:
   for causing a computer to perform the method steps according to claim 1.

14. Method according to claim 5, characterized in that CFR and FFR are calculated during the same period of hyperemia.

* * * * *